US00PP15306P2

(12) United States Plant Patent
Trees

(10) Patent No.: US PP15,306 P2
(45) Date of Patent: Nov. 9, 2004

(54) ***ANGELONIA* PLANT NAMED 'BALANGLOUD'**

(50) Latin Name: *Angelonia augustifolia*
Varietal Denomination: Balangloud

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/740,729

(22) Filed: Dec. 19, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct cultivar of *Angelonia* plant named 'Balangloud', characterized by its white-colored flowers, medium green-colored foliage, and upright and spreading growth habit.

1 Drawing Sheet

Latin name of genus and species of plant claimed: *Angelonia augustifolia.*
Variety denomination: 'Balangloud'.

BACKGROUND OF THE INVENTION

The present invention relates to a new and distinct cultivar of *Angelonia* plant, botanically known as *Angelonia augustifolia* and hereinafter referred to by the cultivar name 'Balangloud'.

The new cultivar was developed by the inventor in a controlled breeding program during February 2000, at Arroyo Grande, Calif. The objective of the breeding program was the development of *Angelonia* cultivars with freely branching and vigorous growth habits, unique flower colors and continuous flowering.

The female parent of the new cultivar was the proprietary *Angelonia augustifolia* selection designated 'BFP-254' (not patented) characterized by its pink-colored flowers, medium green-colored foliage, and freely branching and compact growth habit. The male parent of the new cultivar was the proprietary *Angelonia augustifolia* selection designated 'BFP-272' (not patented) characterized by its white-colored flowers, light green-colored foliage and compact, well branched growth habit. The new cultivar was discovered and selected as a single flowering plant among the progeny of the above cross-pollination by the inventor during March 2001, at Arroyo Grande, Calif. and was initially designated '407-8'.

Asexual reproduction of the new cultivar by terminal stem cuttings since March 2001 at Arroyo Grande, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly it is possible that the phenotype may vary somewhat with variations in environment, such as temperature, light intensity, and day length without, however, any variance in genotype.

It was repeatedly found that the cultivar of the present invention:

1. Exhibits white-colored flowers,
2. Forms medium green-colored foliage, and
3. Exhibits a semi-upright, well branched growth habit.

Plants of the new cultivar differ from plants of the female parent primarily in flower color and from plants of the male parent primarily in foliage color.

Of the many *Angelonia* cultivars know to the inventor, the most similar to 'Balangloud' is 'Anwhit' (U.S. Plant Pat. No. 13,179). However, in side-by-side comparisons, plants of the new cultivar differ from plants of 'Anwhit' in the following characteristics:

1. The plants of the new cultivar are shorter than the plants of 'Anwhit'.
2. The flowers of the new cultivar are smaller than the flowers of 'Anwhit'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from color values cited in the detailed description which accurately describe the colors of 'Balangloud'. The plants were grown in 10 cm pots for 10 weeks in a greenhouse at West Chicago, Ill.

FIG. 1 illustrates a side view of the overall growth and flowering habit of 'Balangloud'.

FIG. 2 illustrates a close-up view of an individual leaf of 'Balangloud'.

FIG. 3 illustrates a close-up view of a single flower of 'Balangloud'.

DETAILED BOTANICAL DESCRIPTION

The chart used in the identification of colors described herein is The R.H.S. Colour Chart of The Royal Horticultural Society, London, England, 1995 edition, except where color terms of ordinary significance are used. The color values were determined on May 14, 2003. The readings were taken between 1:00 and 3:00 p.m. under natural day light conditions. The plants were produced from cuttings taken from stock plants and were grown in a double polycarbonate-covered greenhouse under conditions comparable to those used in commercial practice. The plants were grown in 10 cm pots for 13 weeks while utilizing a soilless growth medium. Greenhouse temperatures were maintained at approximately 65°–75° F. (18°–24° C.) during the day and approximately 50°–60° F. (10°–15° C.) during the night. Greenhouse light levels were maintained at approximately 4,000 to 7,000 footcandles during the day.

Botanical classification: *Angelonia augustifolia,* cultivar 'Balangloud'.

Parentage:

*Female parent.*—Proprietary *Angelonia augustifolia* selection designated 'BFP-254' (not patented).

*Male parent.*—Proprietary *Angelonia augustifolia* selection designated 'BFP-272' (not patented).

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Habit of growth.*—Moderately vigorous with good branching. An average 15 flowering branches develop after pinching.

*Form.*—Upright and outwardly spreading.

*Size.*—A mature plant, 13 weeks after the planting of a rooted cutting, commonly measures approximately 38.6 cm in height from soil level to top of foliage and approximately 51.5 cm in diameter (area of spread).

*Branch.*—Quantity per plant: An average of 15 flowering branches. Shape: Tetragonal. Strength: Moderate. Length from soil level to base of raceme: Approximately 30 cm. Diameter: Approximately 2.6 mm. Texture: Glabrous. Internode length at middle of branch: Approximately 3.1 cm. Color: 145A.

*Foliage.*—Type: Simple. Fragrance: None. Arrangement: Opposite. Orientation to stem: Close to 90°. Shape: Lanceolate. Margin: Serrate. Apex: Accuminate. Base: Decurrent. Length of leaf taken from middle of branch: Approximately 5.8 cm. Leaf width: Approximately 1.4 cm. Texture of upper surface: Sparsely glandular. Texture of lower surface: Glabrous. Venation pattern: Pinnate. Color of mature foliage: Upper surface: 139A with venation of 145B. Lower surface: 146A with venation of 145B.

Flowering description:

*Flowering habit.*—Freely flowering.

*Natural flowering season.*—Year round in greenhouse environment and spring through autumn in outdoor garden.

*Inflorescence type/description.*—Racemes. Length: 18.8 cm. Width: 4 cm. Number per plant: Approximately 15 open racemes per plant. Number of fully open flowers per raceme at any one time: Approximately 11.

*Lastingness of bloom.*—Flowers last approximately 7 to 10 days.

Flower description:

*Type.*—Solitary, zygomorphic, bi-labiate. Flowers have a slight sweet fragrance and are persistent.

*Flower size/aspect.*—Length: Approximately 2.1 cm. Width: Approximately 1.5 cm. Depth: Approximately 7.4 mm. Aspect: Facing outward.

*Petals.*—Quantity: Five per flower, fused at base forming a shallow gullet and the free portions forming an upper lip having two lobes and a lower lip with three lobes.

*Upper lip.*—Lobe apex: Obtuse. Lobe margin: Entire. Length of lobes: 5 mm. Width of lobes: 7 mm. Color of upper surface: 155B. Color of lower surface: 155B. Texture of upper and lower surface: Glabrous.

*Lower lip.*—Lobe apex: Obtuse. Lobe margin: Entire. Length of lobes: 7 mm. Width of lobes: 8 Color of upper surface: 155B. Color of lower surface: 155B. Texture of upper surface: Moderate glandular pubescence at base. Gland color: 2C, transparent. Texture of lower surface: Glabrous.

*Petal color.*—When first opening and when fully opened, the upper surface of all lobes is 155B. Palate on lower lip: 145A. Lower surface is lighter than 155D.

*Gullet.*—Length: Approximately 7 mm. Width: Approximately 5 mm. Depth: Approximately 3 mm. Texture of both surfaces: Glabrous. Color of inner surface: 145B. Color of outer surface: 145C.

*Pedicel.*—Length: Approximately 1.1 cm. Diameter: Approximately 1 mm. Angle to stem. Acute. Strength: Good. Texture: Glandular. Color: 146C.

*Bud.*—Shape: Ovoid. Diameter: Approximately 6 mm. Color: 157C.

*Sepals.*—Five, fused at base. Shape: Lanceolate. Margin: Entire. Apex: Acute. Length: Approximately 4 mm. Width: Approximately 2 mm. Texture: Upper and lower surface: Glabrous. Color: Both surfaces: 144B.

*Reproductive organs.*—Androecium: Stamen quantity: Four per flower. Stamen length: Approximately 3 mm. Filament length: Approximately 2 mm. Filament color: 155B. Anther length: 2 mm. Anther color: 155D. Amount of pollen: Moderate. Pollen color: 11D. Gynoecium: Pistil quantity: One per flower. Pistil length: 4 mm. Stigma length: 0.5 mm. Stigma color: Colorless, transparent. Style length: 2.5 mm. Style color: 155B. Ovary diameter: 1 mm. Ovary color: 145A.

Seed and fruit production: Neither seed nor fruit production has been observed.

Disease and pest resistance: Resistance to pathogens and pests common to *Angelonia* has not been observed.

Hardiness zone: 'Balangloud' is hardy in zones nine (9) and above.

What is claimed is:

1. A new and distinct cultivar of *Angelonia* plant named 'Balangloud' substantially, as herein shown and described, which:

1. Exhibits white-colored flowers,
2. Forms medium green-colored foliage, and
3. Exhibits an upright and spreading growth habit.

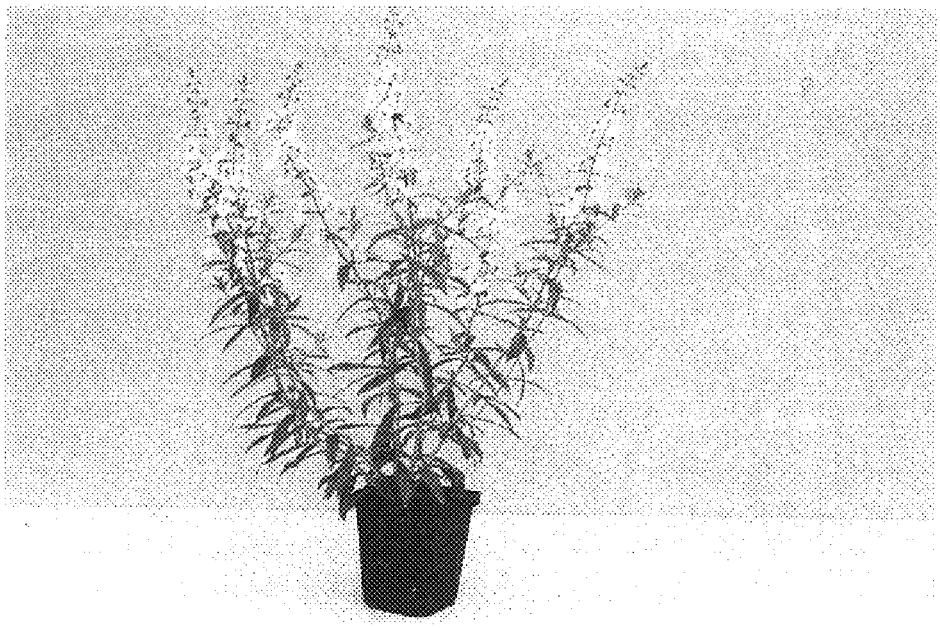
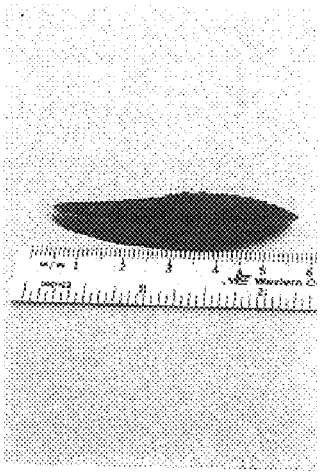
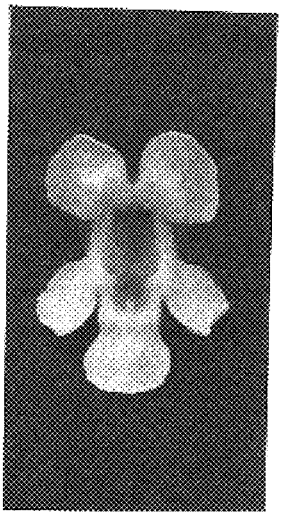

* * * * *